US00PP15463P3

(12) United States Plant Patent
Redman

(10) Patent No.: US PP15,463 P3
(45) Date of Patent: Jan. 4, 2005

(54) ***CHRYSANTHEMUM* PLANT NAMED 'SWING TIME YELLOW'**

(50) Latin Name: *Chrysanthemum morifolium*
Varietal Denomination: Swing Time Yellow

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 10/365,163

(22) Filed: Feb. 11, 2003

(65) Prior Publication Data

US 2004/0158908 P1 Aug. 12, 2004

(51) Int. Cl.[7] ..... A01H 5/00
(52) U.S. Cl. ..... Plt./295
(58) Field of Search ..... Plt./295, 296

(56) References Cited

U.S. PATENT DOCUMENTS

PP12,991 P2 9/2002 Noodelijk ..... Plt./295

OTHER PUBLICATIONS

Brummitt, 1997. The Garden, Horticultural Science: *Chrysanthemum* once again, pp. 662–663.*

U.S. Plant patent application Publication No. 2003/0009810 P1, pub. date Jan. 9, 2003, Appl. No. 09/900,239 filed Jul. 6, 2001, for variety 'Swing Time Dark,' inventor Mark Roland Boeder.

2001 Ficor Catalog listing variety 'Virunga Yellow.' See, e.g., p. 4.

2002 Ficor Catalog listing variety 'Virunga Yellow.' See, e.g., p. 4.

* cited by examiner

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Swing Time Yellow,' having golden yellow single flowers with a flat capitulum form. The new variety has a medium vigor, free branching habit and good foliage presentation.

1 Drawing Sheet

Latin name of the genus and species: Botanical classification: *Chrysanthemum morifolium.*

Variety denomination: The new *Chrysanthemum* variety denomination is 'Swing Time Yellow.'

BACKGROUND OF THE INVENTION

The present invention comprises a new and distinct cultivar of *Chrysanthemum* botanically known as *Chrysanthemum morifolium,* and referred to by the cultivar name 'Swing Time Yellow.' 'Swing Time Yellow,' identified as 20230-6, originated as a naturally occurring whole plant mutation grown in a controlled planting of the variety 'Swing Time Dark' (U.S. Plant patent application Publication No. U.S. 2003/0009810), in Chichester, West Sussex, United Kingdom. The new variety 'Swing Time Yellow' has been asexually reproduced by vegetative cuttings in Chichester, West Sussex, United Kingdom and the distinguishing characteristics are retained through successive generations of asexual reproduction.

BRIEF SUMMARY OF THE INVENTION

'Swing Time Yellow' is a pot type of *Chrysanthemum* plant variety having golden yellow single flowers.

Comparison with Parent

Plants of the new *Chrysanthemum* variety 'Swing Time Yellow' are similar to the parent 'Swing Time Dark' in plant habitat and growth rate. In side-by-side comparisons in Chichester, West Sussex, United Kingdom, under commercial practice, plants of the new *Chrysanthemum* variety 'Swing Time Yellow' compared to the plants of the parent 'Swing Time Dark' in the following characteristics.

1. The new variety 'Swing Time Yellow' produces yellow single flowers whereas the parent 'Swing Time Dark' produces deep orange single flowers.
2. Plants of the new variety 'Swing Time Yellow' have similar inflorescence to plants of the parent 'Swing Time Dark'.

Comparison with Other Varieties

Plants of the new *Chrysanthemum* variety 'Swing Time Yellow' are similar to 'Virunga Yellow' (U.S. Plant Pat. No. 12,991), in plant habitat and growth rate. However, in side-by-side comparisons in Chichester, West Sussex, United Kingdom, under commercial practice, plants of the new *Chrysanthemum* variety 'Swing Time Yellow' differed from plants of 'Virunga Yellow' in the following characteristics.

1. The new variety 'Swing Time Yellow' produces golden yellow single flowers whereas 'Virunga Yellow' produces yellow single flowers.
2. Plants of the new variety 'Swing Time Yellow' have smaller and shorter inflorescence than plants of 'Virunga Yellow'.

BRIEF DESCRIPTION OF ILLUSTRATION

Typical specimens of the plant and flowers for the new *Chrysanthemum* variety 'Swing Time Yellow' are shown in the accompanying digital photograph. The colors shown are as true as possible within the usual limits of this kind of illustration.

FIG. 1 is a whole plant view of the new variety 'Swing Time Yellow' grown in a pot. The plant shown in the illustration is 56 days from the commencement of Short Days.

DETAILED BOTANICAL DESCRIPTION

The following description of the new *Chrysanthemum* variety 'Swing Time Yellow' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 21 days with a response time of about 7.5 weeks. The new variety is suitable for growth in a temperature range of 15° C. to 25° C.

The new variety may be produced as a spray. The following description is with respect to a plant produced as pot *Chrysanthemum*. In the description of this new *Chrysanthemum* variety, color values have been taken from The Royal Horticultural Society Colour Chart (R.H.S.C.C.).

Plant

Plant type: Pot
Habit: Upright
Height: 24 cm
Width: 32 cm
Branching characteristics: Upright and free branching
Length of lateral branches: 16 cm
Diameter of lateral branches: 0.5 cm
Surface of lateral branches: Slightly pubescent
Number of breaks from pinch: 5
Stem color: 137C
Response time: 52 days
Vigor: Medium
Shelf life: 21 days
Disease/pest (susceptibility/resistance observed): None observed to date
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 12
Compound or single: Single
Arrangement of leaves: Alternate
- *Shape of leaf.*—Typically 5 lobed.
- *Size of leaf.*—Width (cm) 5 cm. Length (cm): 7 cm.
- *Leaf apex.*—Rounded.
- *Base.*—Cordate.
- *Attachment.*—Petioled.
- *Aspect.*—Slightly undulating.
- *Margin.*—Lobed.
- *Surface characteristics.*—Top: slightly pubescent. Bottom: pubescent.

Petiole:
- *Color.*—137C.
- *Length.*—2 cm.
- *Diameter.*—0.2 cm.
- *Surface.*—Slightly pubescent.

Venation: Net prominent mid vein at underside
- *Color.*—Upper side: near 137B. Under side: near 137D.

Color:
- *Mature leaf, upper side.*—Near 137A; under side: near 137D.
- *Young leaf, upper side.*—Near 138A; under side: near 137C.

Flower

Flower appearance: Matte
Flower type: Single
Flower form: Slightly cupped
Flower shape: Round
Flowering habit: Flat capitulum
Number of blossoms per branch: 4
Inflorescence form: Cyme
- *Depth of fully expanded blossoms.*—2 cm.
- *Diameter of fully expanded blossoms.*—6 cm.

Phyllaries:
- *Number.*—25.
- *Color.*—Near 137B.
- *Length.*—0.8 cm.
- *Width.*—0.3 cm.
- *Texture/appearance.*—Pubescent.

Peduncle: Peduncle length is shortest at the terminal flower and progressively longer moving down the stem.
- *Length.*—10 cm (average).
- *Diameter.*—0.5 cm.
- *Color.*—Near 137B.
- *Surface.*—Slightly pubescent.
- *Habit.*—Slightly curving.
- *Strength.*—Moderately strong.

Pedicel:
- *Length.*—Terminal: 4 cm; lateral: 5 cm.
- *Color.*—Near 137B.
- *Diameter.*—0.2 cm.
- *Surface.*—Slightly pubescent.
- *Habit.*—Slightly curving.
- *Strength.*—Moderately strong.

Ray florets:
- *Form/shape.*—Straight and spatulate with oblong shape.

*Texture/appearance.*—Matte.
*Number per flower.*—32.
*Length.*—4 cm; Width: 0.8 cm.
*Apex.*—Rounded.
*Base.*—Tapered.
*Margin.*—Entire.

Disc florets:
*Form/shape.*—Cylindrical.
*Texture/appearance.*—Shiny.
*Number per flower.*—150.
*Length.*—0.4 cm; Width: —0.1 cm.
*Diameter of disc.*—1.5 cm.

Fragrance: None observed

Flower bud (at onset of color):
*Length.*—1 cm.
*Diameter.*—1 cm.
*Form/shape.*—Globular.

General flower color:
1. *Ray florets, upper side:* 24B. Immature: near 24A. Mature: near 24B. Older/Fading: near 24C.
2. *Ray florets, under side.*—24B. Immature: near 24B. Mature: near 24B. Older/Fading: Near 24C.
3. *Disc florets.*—Immature: near 151B. Mature: near 151B. Older/Fading: near 21C.
4. *Bud.*—19A.

Flower progression with age: Flower form does not change but there is a slight color fading with age.

Lastingness of blooms: About 21 days.

Reproductive Organs

Gynoecium: Present on Ray and Disc florets.

Ray florets per individual flower:
*Pistil number.*—32.
*Stigma color.*—Near 6C.
*Stigma shape.*—Forked.
*Style color.*—Near 6C.
*Style length.*—0.4 cm.

Disc florets per individual flower:
*Pistil number.*—130.
*Stigma color.*—Near 6C.
*Stigma shape.*—Forked.
*Style color.*—Near 6C.
*Style length.*—0.4 cm.

Androecium: Not observed.

Fruit and Seeds: None observed.

What is claimed is:

1. A new and distinct variety of *Chrysanthemum* plant, substantially as described and illustrated herein.

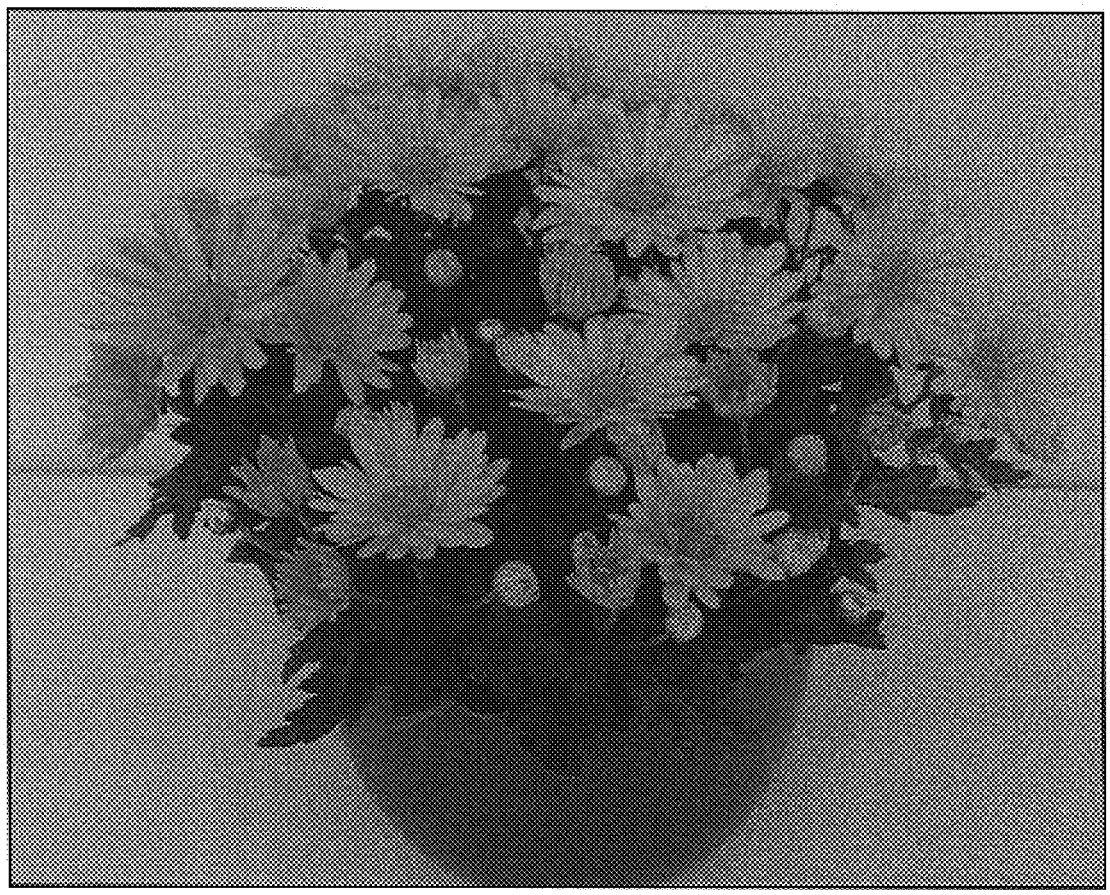

* * * * *